United States Patent [19]

Vansant et al.

[11] Patent Number: 4,999,175

[45] Date of Patent: Mar. 12, 1991

[54] PROCESS FOR SELECTIVE ADSORPTION OF SULFUR COMPOUNDS FROM GASEOUS MIXTURES CONTAINING MERCAPTANS

[75] Inventors: Etienne Vansant, Zoersel; Guido Peeters, Antwerp; Paul de Bievre, Kasterlee; Remi van Gompel, Geel, all of Belgium

[73] Assignee: European Atomic Energy Community (EURATOM), Luxembourg, Belgium

[21] Appl. No.: 352,144

[22] Filed: May 15, 1989

Related U.S. Application Data

[63] Continuation-in-part of Ser. No. 823,994, Jan. 29, 1986, abandoned.

[30] Foreign Application Priority Data

Feb. 1, 1985 [EP]  European Pat. Off. ........ 85200128.8

[51] Int. Cl.$^5$ .......................... B01J 8/00; C01B 17/00; C01B 17/16; C01B 31/20
[52] U.S. Cl. .................... 423/244; 423/230; 423/243; 423/245.1
[58] Field of Search ............... 423/243, 244 A, 244 R, 423/242 A, 242 R, 245.1, 230

[56] References Cited

U.S. PATENT DOCUMENTS

| | | | |
|---|---|---|---|
| 2,818,323 | 12/1957 | Haensel | 23/2 |
| 3,391,988 | 7/1968 | Friess | 23/2 |
| 4,119,404 | 10/1978 | Price | 23/232 E |
| 4,283,373 | 8/1981 | Frech et al. | 423/226 |

OTHER PUBLICATIONS

Butwell, K. F., D. J. Kubek and P. W. Sigmund, "Alkanolamine Treating" in *Hydrocarbon Processing*, Mar. 1982, pp. 108–116.

*Primary Examiner*—Gregory A. Heller
*Attorney, Agent, or Firm*—Weingarten, Schurgin, Gagnebin & Hayes

[57] ABSTRACT

A process for separating sulfur-containing compounds other than mercaptans from gaseous streams. A gaseous stream including mercaptans and other sulfur-containing compounds is brought into contact with a solid supporting material coated with a thin layer of an amine-containing active agent capable of selectively adsorbing the sulfur-containing compounds other than mercaptans. This process permits the monitoring of mercaptans in gaseous streams without interference from other sulfur-containing compounds, as well as the purification of mercaptans.

7 Claims, No Drawings

PROCESS FOR SELECTIVE ADSORPTION OF SULFUR COMPOUNDS FROM GASEOUS MIXTURES CONTAINING MERCAPTANS

This is a continuation-in-part of application Ser. No. 823,994, filed Jan. 29, 1986, which is now abandoned.

In measuring continuously the concentration of polluting agents in air, a high selectivity of the applied equipment is required, since this will determine what exactly is measured. In many cases however, interference by other compounds, disturbing the measurements, is possible. Therefore each detection method has to be tested on its selectivity.

Several specific detection methods are based on physico-chemical properties of a group of compounds, such as sulfur-, nitrogen- or halogenated compounds etc. By using analytical instruments, such as gas or liquid chromatographs and mass spectrometers the individual components within a group can be separated, identified and quantified. In permanent monitoring however, without preceding analysis, these components are frequently measured together in group. High selectivity within one group is hard to obtain, since these components show very similar chemical and/or physical properties.

So for example, a sulfur monitor will detect $SO_2$, COS, $H_2S$, $CS_2$ and RSH together. Separate $SO_2$ scrubbers are commercially available, but quantitative measurement of mercaptans in ppb concentrations in the presence of $H_2S$, COS, and/or $CS_2$ has not yet been possible in permanent monitoring. Furthermore, the present methods for the removal of polluting S-compounds ($SO_2$, COS, $H_2S$, $CS_2$) in air have many disadvantages. Most of the applied processes today involve treating the flue gas with a slurry of limestone, converting the S-components into sulphites or sulphates which usually must be disposed of. Recently a new flue gas desulfurisation process was developed (Mark, 13A process) by Langenkamp and Van Velzen (European Patent No. 16,290). However, all the desulfurisation processes today are very expensive and require high installation costs.

Some industrial processes use ethanolamines in the liquid phase for the removal of acidic gases, such as $H_2S$ and $CO_2$. The two amines which are mainly used are monoethanolamine (MEA) and diethanolamine (DEA), but also others have been applied for gas purification, such as for example the diisopropanolamine (Adip, Sulfinol, SCOT processes).

One of the best known processes is the SNPA-DEA process, developed by the Société Nationale des Pétroles d'Aquitaine of France (Canadian Patent No. 651,379) using aqueous solutions of diethanolamine for treatment of refinery gases, containing COS and $CS_2$ next to $H_2S$ and $CO_2$.

The concentrated aqueous DEA solutions adsorb acid gases up to the stoichiometric molar ratio, typically 1.0 to 1.3 mole of DEA per mole of acid gas, provided the partial pressure of the acid gas in the feed gas is sufficiently high. The residual gas stream however still contains around 5 ppm of $H_2S$, which may be satisfactory for several applications, but which is still 4 orders of magnitude larger than the level required for monitoring mercaptans which should not be interfered by $H_2S$ or $CS_2$. There is no selectivity of DEA for S-compounds in its aqueous or other solutions in the ppb or ppm concentrations. On a large industrial scale, most of the mercaptans are not retained by a DEA column, but always small amounts are trapped because of their physical solubility. Because of their low concentrations in the feed gas, the poor selectivity at low concentrations and the still remaining ppm concentrations of other S-compounds in the purified gas stream, pure ethanolamines or their solutions are not suitable for quantitative separation down to ppb's of mercaptans from $H_2S$ and $CS_2$.

U.S. Pat. No. 2,818,323 of Haensel discloses amine-impregnated solid absorbents for the removal of acidic gases such as $H_2S$, $CO_2$ and $SO_3$ from gas streams. Among the solid absorbents listed are silica gel and alumina. Diethanolamine and dipropanolamine are mentioned as appropriate amines. A large quantity of the amine is applied to the solid material by soaking, spraying or other techniques. In practice, the gas stream to be treated is brought into contact with the amine-coated absorbent, which is then regenerated and recycled back into the treatment process. Mercaptans are not specifically mentioned in the reference, but as these materials are generally considered to be acidic, they would be expected to be removed, at least in part, by a treatment process employing the disclosed absorbent.

U.S. Pat. No. 3,391,988 of Friess discloses a process for the removal of mercaptans from gaseous streams by oxidizing them in the presence of free oxygen with a solid absorbent impregnated with a liquid mixture of an alkaline material, then passing the disulfide-containing gas stream to an adsorbent for disulfides. Among the various alkaline liquids disclosed are a number of alkanolamines, which are applied to the solid support, either full strength as the liquid, or in solution. The alkaline liquid also contains a thickening agent. This reference appears to disclose that mercaptans are absorbed, or at least sufficiently retarded, by contact with an alkanolamine-coated solid material, to permit a subsequent oxidation to disulfide to occur.

U.S. Pat. No. 4,283,373 of Frech discloses that metal salts of sulfonamides on a carrier, or resins containing sulfonamide functionalities, are capable of removing sulfur compounds from gas streams. It further discloses in its background section that various prior art processes involving physical absorption, solid adsorption, or chemical processes do not remove mercaptans, sulfides, and disulfides efficiently.

An article by Butwell et al., published in "Hydrocarbon Processing" pp. 108–116 in 1982, discusses the treatment of gaseous streams with alkanolamines and discloses that methyl mercaptan behaves like a weak acid and is removed from a gas stream to a significant extent by alkanolamines. Mercaptans having longer hydrocarbon chains are stated to have less acidic character and more hydrocarbon character, and are therefore less efficiently removed by alkanolamines than methyl mercaptan.

The prior art has not disclosed or suggested that amine-containing adsorbing systems can be prepared which remove from gaseous streams sulfur-containing compounds such as $H_2S$, COS, $SO_2$, and $CS_2$, etc. while simultaneously not removing mercaptans.

The present invention is directed to a process for separating other sulfur compounds from a gaseous mixture containing one or more mercaptans, and other sulfur compounds.

For purpose of this application, the phrase "ppb range" means ten's to hundred's of parts per billion, the language "ppm range" means one's to ten's of parts per millions, and the language "percent range" means tenth's of a percent and higher.

Surprisingly it has been found, it is possible to treat such a gaseous mixture with an impregnated solid material suitable for the selective adsorption of sulfur compounds comprising a solid material which has been impregnated with an active agent for the said selective adsorption.

Such a process can be applied for a permanent monitoring of mercaptans (even in ppb concentrations), in a matrix containing $H_2S$, COS, $CS_2$ and $SO_2$, without the use of an additional scrubber, or for an ultra-purification of commercial RSH products, or for an efficient removal of $SO_2$, $H_2S$, $CS_2$ and COS from air. With this invention, impregnated solids can be manufactured which are highly efficient for the capture of $NO_X$, so that simultaneously a complete removal of sulfur and nitrogen-containing polluting agents can be obtained. The technical and economical advantages of the desulfurisation method, compared with mostly used processes are the following: (a) low installation and product costs, (b) very high removal efficiencies for $H_2S$, $SO_2$, $CS_2$ and COS, (c) potential for a continuous operation. Furthermore, the same technique can be used for the removal of $NO_X$.

Some of the solids which can be used for the impregnation treatment are silicagel, alumina, clay minerals, zeolites and mixtures thereof. The active agents for the impregnation procedure, which have been found to be effective are amines, amine complexes or their derivatives. For the impregnation procedure, the solid is mixed homogeneously with the active agents at temperatures between 0° C. and 200° C. The loading of the solid material can be controlled by the initial amount of the active agent in contact with the solid. Afterwards, the mixture can be thermally treated (below 300° C.) and dried in air or in an inert atmosphere. This thermal treatment determines the ultimate loading of the active agent on the solid. After a reconditioning of the impregnated material (flow or dry inert gas), the material becomes activated. This process creates the high selectivity. The selectivity of the impregnated solid for $SO_2$, COS, $CO_2$, $NO_X$, $H_2S$ is the result of various types of reactions. For $CS_2$ the selectivity is governed by

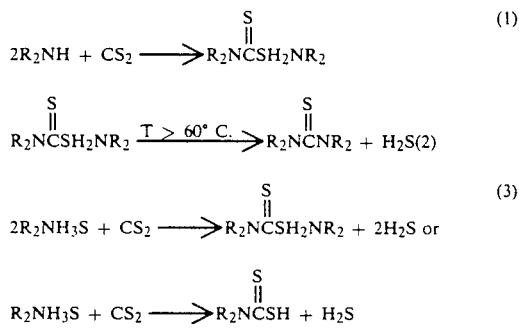

Similar reactions can be obtained for the selectivity of COS, $SO_2$, $CO_2$, $NO_X$.

For $H_2S$ the selectivity is the result of the reaction

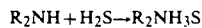

Because the external surface of the impregnated material is covered by agents which are inactive for mercaptans (RHS) no reactions or adsorption phenomena occur for the RSH type compounds.

According to the present invention, the impregnated solid has a very high selectivity for $H_2S$, $CS_2$, $SO_2$ and COS, so that in a mixture of $H_2S$, $SO_2$, $CS_2$, COS and RSH, the components $H_2S$, $CS_2$, $SO_2$ and COS can be captured quantitatively after which mercaptans (RHS) can be determined quantitatively with a universal S-monitor.

This quantitative behaviour is observed in the %, ppm and ppb range of the different S-compounds in a mixture.

Other gaseous components such as $O_2$, $N_2$, CO, $H_2O$, air etc. have no significant effect on the efficiency of the impregnated solid and have therefore no impact on the quantitative capturing of the S-compounds.

This invention accordingly provides a selective solid which enables for the first time a permanent monitoring of mercaptans in a matrix containing $H_2S$, $SO_2$, COS, $CS_2$ with a conventional S-monitor. Furthermore it also allows an ultra-purification of commercial RSH products or a high efficient simultaneous desulfurisation ($SO_2$, $H_2S$, $CS_2$ and COS) and denitrogenation ($NO_X$) of a flue gas from the combustion of fossil fuels (containing sulfur).

As discussed above, the adsorbent compositions of the invention are solid materials coated with controlled amounts of adsorbing materials, these adsorbing materials generally being certain amines or complexes of amines with metals.

In principle, any solid material capable of adsorbing amines and having either a substantially nonporous structure or a porous structure with preferably relatively large pores will serve as the solid material on which the adsorbing material is to be coated. In the event that the solid supporting material is porous, it has preferably average pore diameters in the range 2 to 100 Å, preferably 5 to 95 Å.

If the solid supporting material is porous, the minimum pore size is i.a. determined by the sizes of the molecules in the gas to be treated.

The molecules of the gas to be treated must be able to pass through the porous solid material in its coated state. The pores must be of a sufficient size that they are not completely filled by the adsorbing material at the loading level employed, thereby causing bulk coating effects.

The surface area, and in the case of porous supporting materials, the pore size of the solid supporting material, are also important considerations.

Examples of suitable solid materials are silica, alumina, clay minerals and zeolites.

The adsorbing material should be substantially unreactive with mercaptans, but reactive with other sulfur-containing materials such as $SO_2$, $H_2S$, COS, $CS_2$, thiophene, and various thionaphthalenes, which may be present in gas streams to be treated.

One class of adsorbing materials is alkyl amines and diamines. Primary alkyl amines and diamines such as ethylene diamine are superior to secondary alkyl amines, which in turn are superior to tertiary alkyl amines in terms of their lack of reactivity with mercaptans and their relatively good reactivity with $H_2S$, $CS_2$, COS, $SO_2$, etc. The relatively high vapor pressure of alkyl amines causes the compositions of solid materials coated with these materials to have use temperatures which are relatively low, about room temperature. These compositions are also subject to attack by water, which can displace certain of these amines from the solid material. A further difficulty with the use of alkyl amines is that they are generally not highly efficient in removing sulfur-containing materials from gases. Compositions containing alkyl amines are generally useful for treatment of gases having sulfur-containing compounds present in the percent range, but are less useful for gases having sulfur-containing compounds present in the ppb range.

Alkanolamines are generally superior to alkyl amines for removing sulfur-containing compounds from gaseous streams while leaving mercaptans. They may be employed as the adsorbing material when the gas stream to be treated includes sulfur-containing materials at the percent, ppm or ppb range. Compositions of alkanolamines coated on solid supporting materials are in general more stable than similar compositions including alkyl amines since the hydroxyl groups of the alkanolamines cause these materials to possess lower vapor pressures than the corresponding alkyl amines. Compositions of alkanolamines on solid supporting materials therefore possess higher use temperatures than similar compositions containing alkyl amines.

Compositions containing secondary alkanolamines, e.g., diethanolamine, have stabilities superior to those containing primary alkanolamines because of the lower vapor pressures of the secondary alkanolamines. Compositions containing primary or secondary alkanolamines are also generally superior to compositions containing tertiary alkanolamines, e.g., triethanolamine, because the tertiary alkanolamines have relatively poor reactivities with sulfur-containing components of the gas being treated. Compositions containing secondary alkanolamines are particularly useful for gases having sulfur-containing compounds in the ppb range, and these compositions of secondary alkanolamines on solid supporting materials are generally superior to similar compositions containing primary alkanolamines. Thus, compositions of diethanolamine on solid supporting materials are generally superior to similar compositions containing monoethanolamine or triethanolamine. For treatment of gases containing the lowest levels of sulfur-containing materials, and for most analytical work, compositions of diethanolamine on solid supporting materials are preferred. Compositions including other adsorbing materials can be used, however, for the treatment of gaseous streams containing higher levels of sulfur-containing materials.

Complexes of alkyl amines or alkanolamines with metals such as copper, nickel, cobalt, and iron, etc. may also be employed as the adsorbing material to be coated on the solid-supporting material.

The loading of the adsorbing material on the solid-supporting material is an important factor in forming compositions having the desired selective properties. The solid supporting material must be coated with at least the molecular monolayer of the adsorbing material, to prevent interaction of sulfur-containing compounds with the surface of the solid supporting material. On the other hand, the loading of the absorbing material on the solid supporting material must not be so high that the coating begins to behave like the bulk material and diffusion effects start to operate.

The loading of the solid material will generally be between 1 and 10 mmol of the adsorbing material per gram of solid material. Preferably this loading will be between 4.5 and 8 mmol/g, as within this range the greatest ease of operation is obtained, especially in monitoring operations.

Regarding the effect of the concentration of sulfur-containing compounds in the gas to be treated, higher loadings of adsorbing materials are required for higher levels of sulfur-containing compounds in the gas.

A preferred adsorptive composition employs silica having an average pore diameter between 50 and 75 Å as the solid supporting material, diethanolamine as the adsorbing material, and a loading of the diethanolamine on the solid supporting material of 4.5–8 mmol of diethanolamine per gram of solid supporting material. This composition is especially useful for monitoring mercaptan concentrations in gaseous streams containing sulfur-containing materials at ppb levels. It has been experimentally demonstrated that using this material, 150 ppb of methyl mercaptan can be measured in the presence of 120 ppb of $H_2S$ by passing a gaseous stream containing these two sulfur-containing materials through a column of an adsorptive composition and measuring the sulfur content of the effluent gas at about 5 minutes after the start of the test. At this time, the methyl mercaptan had broken through the column of adsorptive composition almost completely, while the $H_2S$ had either not as yet broken through, or had just begun to break through. At the time of measurement, therefore, the sulfur concentration in the effluent gas is due entirely, or almost entirely, to methyl mercaptan.

EXAMPLES

In all experiments a 10 cm tube with internal diameter of 0.21 mm, filled with the impregnated solid, was used as a filter. Gas mixtures of S-compounds in He were sent continuously through the filter, while the composition of the effluent was permanently measured by gas chromatography (for >100 ppm concentrations) and with a sulfur monitor for low ppm and ppb concentrations. In this way the selectivity and capacity of SilDEA (silicagel impregnated with diethanolamine) and AlDEA (alumina with DEA) filters were determined. Also $N_2O$, $NO_2$ and $CO_2$ containing gas streams were treated. In addition ethylenediamine (EDA) was tested as coating agent, by forming SilEDA filters.

EXAMPLE 1

A mixture of $H_2S$, MeSH and $CS_2$, 0.1 vol % of each in He was sent through a SilDEA filter at flow rate of 25 ml/min. From the beginning the filtered effluent contained 0.1% MeSH but no $H_2S$ and no $CS_2$. The breakthrough of $H_2S$ was observed after 25 minutes, for $CS_2$ after 5 hours. When the same mixture is sent through untreated silicagel or a liquid DEA solution under similar conditions, no sharp selectivity is obtained. With pure silicagel a large amount of MeSH is adsorbed, but also small amounts of $H_2S$ and $CS_2$. In the DEA solutions larger amounts of all S-compounds were trapped. Only after 10 minutes a slow breakthrough of MeSH was observed, and a few minutes later—before breakthrough of MeSH was obtained—$H_2S$ appeared in the effluent.

EXAMPLE 2

A mixture of $H_2S$, MeSH, $CS_2$, 0.1% of each in He was sent through a SilDEA filter at a flow rate of 25 ml/min. The filter was kept at 0° C. in an ice bath. During 1 hours the effluent contained only 0.1% of MeSH. Then $H_2S$ appeared, but breakthrough of $CS_2$ was not observed within 8 hours.

EXAMPLE 3

A mixture of $H_2S$, MeSH, $CS_2$, 150 ppm of each in He was sent at a flow of 25 ml/min through a SilDEA filter. The effluent contained 150 ppm MeSH, but no $H_2S$ and no $CS_2$.

EXAMPLE 4

A mixture of $H_2S$, MeSH, $CS_2$, 0.1% of each in He was sent at a flow rate of 25 ml/min through an AlDEA filter at room temperature. The effluent contained only 0.1% of MeSH. For $H_2S$ and $CS_2$ breakthrough times of 25 minutes and 6 hours were obtained respectively.

EXAMPLE 5

Mixtures containing n-butyl-mercaptan and iso-butyl-mercaptan were tested on SilDEA and AlDEA filters. No retention of the mercaptans was observed, while $H_2S$ and $CS_2$ were filtered out, quantitatively.

EXAMPLE 6

When air, containing 100 ppb $H_2S$ or 100 ppb $CS_2$ was sent through an AlDEA or SilDEA filter, no signal was obtained on the sulfur monitor, but when air with 10 ppb or mercaptan was passed over the filter, the detector indicated 10 ppb after a few moments. From a mixture of 100 ppb $H_2S$, 100 ppb $CS_2$ and 20 ppb mercaptan, all $H_2S$ and $CS_2$ were removed quantitatively, without retention of any mercaptan, so that 20 ppb was detected on the S-monitor.

EXAMPLE 7

Air was contaminated with 0.1% $H_2S$ and 0.1% $CS_2$, and sent through a SilDEA filter at a flow rate of 25 ml/min. No sulfur components were detected in the effluent during the experiment, which was carried out during about 30 minutes.

EXAMPLE 8

A mixture of 1% $SO_2$ in He was sent through a SilDEA filter at a flow rate of 25 ml/min. The $SO_2$ was filtered out quantitatively during 80 minutes before it appeared in the effluent. In a similar experiment, using pure silicagel, breakthrough of $SO_2$ was observed after a few minutes.

EXAMPLE 9

A mixture of 1% $NO_2$ in He was sent through a SilDEA filter at a flow rate of 25 ml/min. The $NO_2$ was filtered out quantitatively during 68 minutes before it appeared in the effluent. In a similar experiment with 1% $N_2O$ in He, no retention of $N_2O$ was observed. The SilDEA filter therefore is suitable for distinguishing $NO_2$ from $N_2O$ in $NO_x$ measurements. On pure silicagel no selectivity was observed.

EXAMPLE 10

A mixture of 1% $CO_2$ in He was sent through a SilDEA filter at a flow rate of 25 ml/min. During 9 minutes the effluent was free of $CO_2$. When pure silicagel was used for a similar test, no retention of $CO_2$ was observed.

EXAMPLE 11

A mixture of $H_2S$, MeSH, $CS_2$, 0.15% of each in He was sent through a SilDEA (silicagel+ethylenediamine) filter at a flow rate of 25 ml/min. Within the first minutes a breakthrough of MeSH was observed, but $H_2S$ and $CS_2$ were quantitatively retained. After $2\frac{1}{2}$ hours $H_2S$ appeared in the effluent, but after 6 hours the gas stream was still free of $CS_2$.

EXAMPLE 12

The effect of various loadings of diethanolamine on porous silica having an average pore diameter between 50 and 75 Å was studied for DEA loadings between 0 and 6 mmol/g by passing feed gas containing methyl mercaptan through columns of the adsorptive compositions. For feed gas containing a 150 ppm level of methyl mercaptan, it was found that if the DEA loading was below 2 mmol/g, the methyl mercaptan was at first retained but then broke through the column within a few minutes. If the DEA level was above 2 mmol/g, the methyl mercaptan broke through the column essentially immediately. Some methyl mercaptan was adsorbed at 100% breakthrough regardless of loading. With increasing DEA levels above 2 mmol/g, the methyl mercaptan breakthrough became increasingly sharper and the amount of methyl mercaptan which was adsorbed at 100% breakthrough was minimized and remained constant at approximately 10% of the feed level. It was concluded that optimum pass-through of methyl mercaptan occurred at DEA loadings of 5 mmol/g and above.

EXAMPLE 13

In another set of experiments on the same porous silica as used in Example 12 and various loadings of diethanolamine, the ability of a column of this adsorptive composition to adsorb $H_2S$ was measured as a function of the DEA loading level. At DEA loading levels of less than 2 mmol/g, $H_2S$ was not well adsorbed, and the capacity of the adsorbent composition was found to be about 0.01–0.02 mmol $H_2S$ per gram of adsorbent composition. As the loading of DEA was increased from 2 to 5 mmol/g, $H_2S$ adsorption increased to about 0.13 mmol $H_2S$ per gram of adsorbent composition. At and above a loading of 5 mmol of DEA per gram the $H_2S$ adsorption was found to be at maximum and essentially constant. It was concluded that for best $H_2S$ adsorption, the loading of DEA on the silica should be above 5 mmol of DEA per gram of solid supporting material.

EXAMPLE 14

In another set of experiments on the same silica and various loadings of diethanolamine, the effect of the DEA loading on adsorption of $CS_2$ was studied. At DEA loadings less than 2 mmol/g, $CS_2$ was not well adsorbed and was found to break through the column essentially immediately. As the DEA loading was increased from 2 to 5 mmol/g the breakthrough time increased to about 200 minutes. Above a loading of 5 mmol DEA per gram of solid supporting material, the $CS_2$ breakthrough time decreased again, presumably due to the operation of diffusion effects. It was again concluded that the optimum DEA loading for this silica solid supporting material was 5 mmol of DEA per gram or above.

EXAMPLE 15

In tests of the adsorption of $H_2S$ and methyl mercaptan at ppb levels on the same silica and a loading of approximately 6 mmol of DEA per gram, it was found that $H_2S$ at a level of 120 ppb in the feed gas broke through the column starting at about $4\frac{1}{2}$ minutes after the start of the experiment and thereafter the H₂S in the effluent gas rose over approximately 20 minutes to approximately 55 ppb. Methyl mercaptan in the feed gas at a level of about 150 ppb broke through the column immediately and rose quickly to about 135 ppb in the effluent gas at approximately 5 minutes after the start of the experiment and thereafter remained essentially constant. It was concluded that to measure methyl mercaptan in the presence of H₂S at ppb levels, the measurement of the sulfur content of the effluent gas should be made at about 5 minutes after the start of the experiment.

EXAMPLE 16

In a series of experiments testing the effects of various amines coated on both silica and alumina, silica samples were coated with ethylene diamine, diethylamine, and triethylamine. Similarly alumina was coated with monoethanolamine, diethanolamine, and triethanolamine. Feed gases containing 0.1% each of H₂S, methyl mercaptan, and CS₂ were passed through columns of the adsorptive materials. It was found that triethylamine on silica and triethanolamine on alumina both performed relatively poorly for the presently-intended purpose, each of the three test materials breaking through the respective column within a matter of minutes. Ethylene diamine on silica allowed methyl mercaptan to break through almost immediately, 100% breakthrough being reached in approximately 5 minutes. On this column H₂S broke through starting at about 128 minutes, and CS₂ did not break through during the 155 minute period of the test. Monoethanolamine on alumina allowed methyl mercaptan to break through at about 3 minutes into the test, the 100% breakthrough level being reached in about 30 minutes. H₂S first broke through at approximately 220 minutes and CS₂ did not break through during the 250 minutes test period. Diethylamine on silica allowed methyl mercaptan to break through in about 2 minutes, the 100% breakthrough level being reached in about 10-12 minutes. H₂S broke through at about 17 minutes and CS₂ began breaking through at about 33 minutes. Diethanolamine on alumina allowed methyl mercaptan to break through at about one minute, the 100% breakthrough level being reached at about 10 minutes. H₂S began breaking through at about 38 minutes and CS₂ did not break through during the 400 minute test period. The conclusion from these experiments is that primary and secondary alkyl amines and alkanolamines have some utility for the presently intended purpose, but the tertiary alkyl amines and alkanolamines are less well-suited.

We claim:

1. Process for separating other sulfur compounds from a gaseous mixture containing one or more mercaptans, and other sulfur compounds, characterized in that the gaseous mixture is treated with an impregnated solid material suitable for selective adsorption of the sulfur compounds $SO_2$, $H_2S$, $CS_2$, and COS; said impregnated solid material comprising a solid material selected from the group consisting of silica, alumina, clay minerals, zeolites, and mixtures thereof, as well as an active agent selected from the group consisting of monoethanolamine, diethanolamine, ethylenediamine, derivatives of these amines, and metal-containing complexes of these amines and derivatives; said solid material being impregnated with said active agent in an amount from 1 to 10 mmol of active agent per gram of solid material.

2. Process according to claim 1, characterized in that the active agent is chosen from the group consisting of monoethanolamine, diethanolamine and ethylenediamine.

3. Process according to claim 1, wherein the mercaptans are continuously monitored in a matrix gas comprising $SO_2$, $H_2S$, and either $CS_2$ or COS or both, using a sulfur monitor.

4. Process according to claim 1, wherein said amount of active agent is from approximately 5-8 mmol/g of solid material.

5. Process for purifying mercaptan, comprising the step of bringing a gaseous mixture containing mercaptan into contact with an impregnated solid material suitable for selective adsorption of the sulfur compounds $SO_2$, $H_2S$, $CS_2$, and COS; said impregnated solid material comprising a solid material selected from the group consisting of silica, alumina, clay minerals, zeolites, and mixtures thereof, as well as an active agent selected from the group consisting of monoethanolamine, diethanolamine, ethylenediamine, derivatives of these amines, and metal-containing complexes of these amines and derivatives; said solid material being impregnated with said active agent in an amount from 1 to 10 mmol of active agent per gram of solid material.

6. Process according to claim 5, characterized in that the active agent is chosen from the group consisting of monoethanolamine, diethanolamine and ethylediamine.

7. Process according to claim 5, wherein said amount of active agent is from approximately 5-8 mmol/g of solid material.

* * * * *

UNITED STATES PATENT AND TRADEMARK OFFICE
CERTIFICATE OF CORRECTION

PATENT NO. : 4,999,175

DATED : March 12, 1991

INVENTOR(S) : Etienne Vansant, et al.

It is certified that error appears in the above-identified patent and that said Letters Patent is hereby corrected as shown below:

Column 3, line 52, delete "(2)" from the end of the equation; and insert the equation number --(2)-- at the right margin.

Column 5, line 25, "c.g., diethanolamine" should read --e.g., diethanolamine--.

Column 5, line 61, "absorbing" should read --adsorbing--.

Column 7, line 66, "Si1DEA" should read --Si1EDA--.

Signed and Sealed this

Thirtieth Day of March, 1993

Attest:

STEPHEN G. KUNIN

Attesting Officer

Acting Commissioner of Patents and Trademarks